Figure 1:
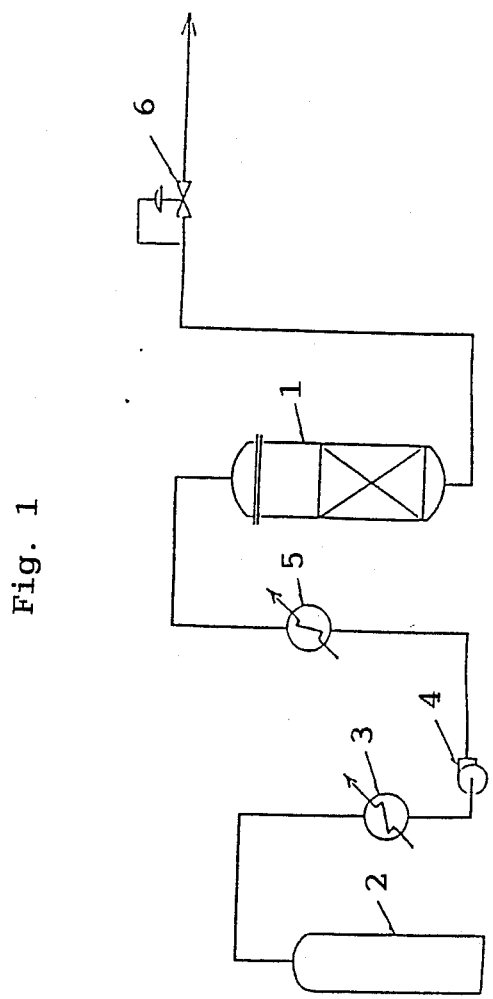

United States Patent [19]

Shimizu et al.

[11] Patent Number: 4,933,334

[45] Date of Patent: Jun. 12, 1990

[54] ANTIBIOTIC COMPOSITION

[75] Inventors: Hisayoshi Shimizu; Yasushi Mikura, both of Osaka; Yasuo Doi, Hyogo, all of Japan

[73] Assignee: Takeda Chemical Industries, Ltd., Osaka, Japan

[21] Appl. No.: 274,977

[22] Filed: Nov. 22, 1988

[30] Foreign Application Priority Data

Dec. 4, 1987 [JP] Japan ................................ 62-308350

[51] Int. Cl.$^5$ ........................................ A61K 31/545
[52] U.S. Cl. ................................................... 514/202
[58] Field of Search ........................................ 514/202

[56] References Cited

U.S. PATENT DOCUMENTS 4,161,527  7/1979  Ishizuka et al. .................... 514/206

FOREIGN PATENT DOCUMENTS 0203271  12/1986  European Pat. Off. ............ 514/202
720580    1/1972  South Africa ....................... 514/200

Primary Examiner—Jerome D. Goldberg
Attorney, Agent, or Firm—Wegner & Bretschneider

[57] ABSTRACT

An antibiotic composition which comprises 7$\beta$-[(Z)-(5-amino-1,2,4-thiadiazol-3-yl)-2(Z)-methoxyiminoacetamide]-3(1-imidazo[1,2-b]pyridazinium)-methyl-3-cephem-4-carboxylate hydrochloride and a pharmaceutically acceptable water-soluble basic substance, which is stable in storage and improved in solubility as well as free of local actions or hemolytic action.

4 Claims, 6 Drawing Sheets

SCE-2787 (HCl)

SCE-2787 (HCl) N,N-Dimethylformamide Solvate

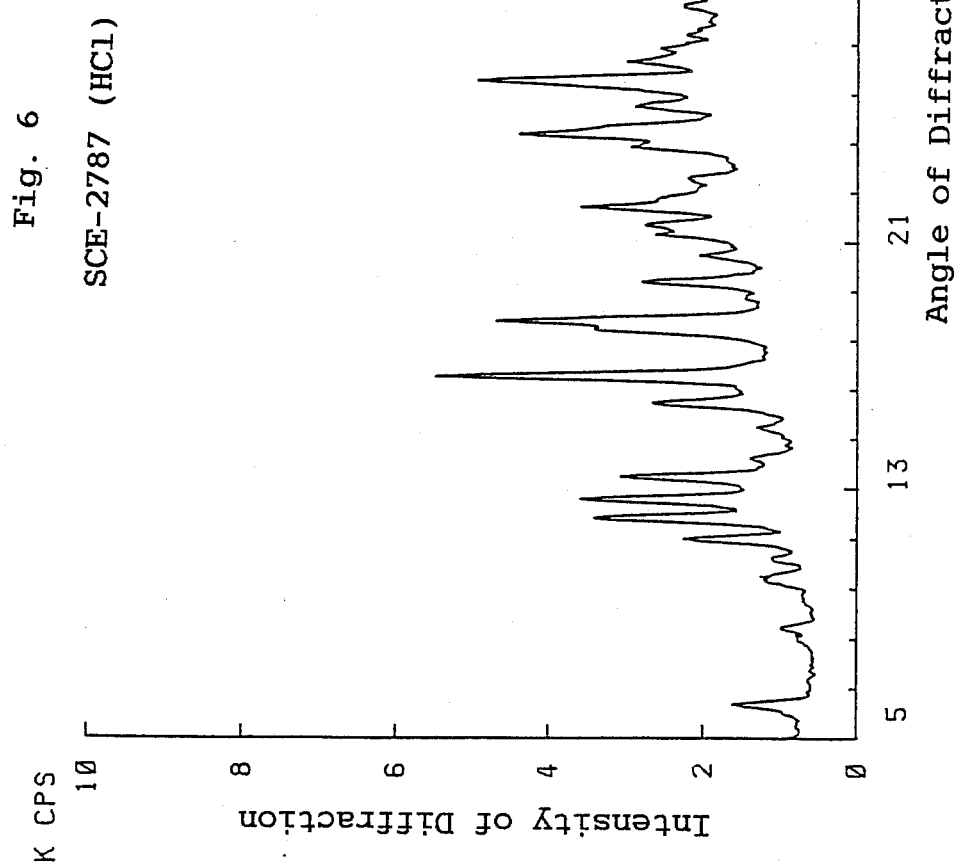

ANTIBIOTIC COMPOSITION

This invention relates to an antibiotic compostion. 7β-[(Z)-2-(5-Amino-1,2,4-thiadiazol-3-yl)-2-methoxyiminoacetamido]-3-(1-imidazo [1,2-9pyridazinium methyl ]-3-cephem-4-carboxylate (hereinafter referred to briefly as SCE-2787) is a useful antibiotic agent described in detail in Japanese Kokai Tokkyo Koho (published unexamined patent application) No. 62-149682 (European Patent Application Laid-Open No. 203271). This compound, having the chemical structure

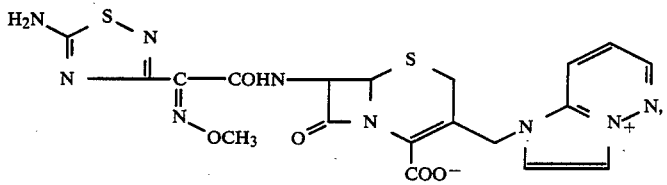

has broad-spectrum and high antibacterial activity against both gram-positive and gram-negative bacteria, inclusive of *Pseudomonas aerucinosa*, and even shows comparatively high effectiveness against infections caused by methicin-cephem-resistant strains of *Staphylococcus aureus* (MRSA) which are of great recent concern.

While SCE-2787 as such is a compound having the above-mentioned excellent antibacterial action, it has certain problems. Thus, it is sparingly soluble in water. Although conversion of SCE-2787 to its hydrochloride [hereinafter referred to as SCE-2787 (HCl), particularly the hydrochloride in the form of crystals, results in improved solubility in water, the rate of dissolution of SCE-2787(HCl) in a solvent, such as distilled water, for injection is still slow as compared with ordinary powder-form injectable medicinal chemicals. Furthermore, even when the dissolution of SCE-2787(HCl) is complete at the time of dissolution, an insoluble matter may precipitate out with the lapse of time, as indicated by the data shown below in the table.

TABLE

| | Change in solubility after dissolution (25° C.) | | |
|---|---|---|---|
| | Concentration of SCE-2787 (HCl) | | |
| Time (hours) | 1 g/100 ml (10 mg/ml) | 1 g/20 ml (50 mg/ml) | 1 g/3 ml (333 mg/ml) |
| 0 | — | — | — |
| 1 | + | +++ | — |
| 2 | ++ | +++ | + |
| 4 | ++ | +++ | + |
| 24 | +++ | +++ | ++ |

(Criteria for solubility evaluation)
−Clear and transparent
+Turbid (fine insoluble matter floating)
++Insoluble matter floating
+++Insoluble matter precipitate Therefore, SCE-2787(HCl) must be administered either immediately after dissolution or in the form of an extremely diluted solution (having a concentration of 1 mg/ml or less). In the former case, crystals might possibly precipitate out during the period between solution preparation in a dispensary and administration of the solution. In the latter case, it is difficult to secure an effective concentration and the volume of the solution to be injected becomes large. Thus, in either case, the situation is very unfavorable from the view-point of preparation of an injectable solution. Improvements are therefore desired. In addition, since SCE-2787(HCl) gives a low pH value, its administration by intramuscular injection might expectedly produce adverse local effects, such as muscle cell necrosis, whitening, browning and bleeding at the site of administration, and/or hemolysis. Improvements are desired in this respect as well. Accordingly, it is an object of the invention to provide pharmaceutical compositions for injection which show an improved solubility of SCE-2787 and/or SCE-2787(HCl) and with which the above-mentioned local effects and hemolytic action can be suppressed.

As a result of their intensive investigations made to solve the above problems, the present inventors unexpectedly found that when SCE-2787(HCl) is used in combination with a pharmaceutically acceptable or nontoxic water-soluble basic substance, the above problems can be overcome simultaneously without impairing the storage stability of SCE-2787(HCl) (from the viewpoints of insoluble matter precipitation and stability of principal active ingredient etc.), namely (1) post-dissolution insoluble matter precipitation never occurs in spite of the fact that SCE-2787(HCl), upon dissolution, is converted to SCE-2787 as a result of neutralization of the HCl component thereof by the nontoxic basic substance and (2) the above-mentioned local actions and hemolytic action disappear. Further investigations based on the above findings have now led to completion of the present invention.

Thus, the invention is concerned with an antibiotic composition characterized by containing 7β-[(Z)-2(5-amino-1,2,4-thiadiazol-3-yl)-2-methoxyiminoacetamido]-3-(1-imidazo[1,2-b]pyridazinium)-methyl-3-cephem-4-carboxylate hydrochloride and a pharmaceutically acceptable water soluble basic substance.

The SCE-2787(HCl) to be used in accordance with this invention is preferably in the form of crystals. It is true that as is often the case with cephalosporins, the crystallization of SCE-2787(HCl), particularly original crystallization, was far from easy. But such a crystalline form is advantageous in terms of purification, handling, purity and so on. Such crystals of SCE-2787(HCl) can be produced, for example, by reacting SCE-2787 with hydrogen chloride in the presence of water and an organic solvent, collecting the resulting precipitate crystals and, if desired, subjecting the crystals to organic solvent elimination (desolvation) procedure for conversion to organic solvent-free SCE-2787(HCl) crystals. Either the amorphous form or the crystalline form of SCE-2787 can be used as the starting material.

In originally crystallizing SCE-2787 (HCl) of the present invention, crystals of SCE-2787 were dissolved in dilute hydrochloric acid, and the solution was concentrated to half the volume, whereto dimethylformamide is added. Acetone was gradually added to the mixture under stimulating at room temperature to give the crystals. By reacting hydrogen chloride with SCE-2787, using the thus obtained crystals as a seed crystal, crystallization of SCE-2787 (HCl) has been enabled under a wide variety of conditions.

The starting material in practicing the invention, namely SCE-2787, can be produced in the amorphous form, for example by the procedure described in the above-cited Japanese Kokai Tokkyo Koho No. 62-149682 (EPA Laid-Open No. 203271), in particular in Example 13 therein.

In the method for producing SCE-2787 (HCl) employing organic solvents, SCE-2787 crystals can be produced by dissolving an amorphous powder of SCE-2787 in a small amount of water or by purifying and concentrating such powder in the conventional manner. They can be produced also by neutralizing an aqueous solution of SCE-2787(HCl) with an alkali such as sodium hydrogen carbonate.

Generally, SCE-2787 (amorphous or crystalline) is reacted with one equivalent or more (desirably from the economical viewpoint, up to about 5 equivalents, although there is no upper limit) of hydrogen chloride in the presence of 0.1 part by weight or more (preferably from the economical viewpoint, up to about 10 parts by weight, although there is no upper limit), desirably 1-5 parts by weight of water relative to one part by weight of SCE-2787 and in the presence of about 1 to 10 times the amount of water used of an organic solvent. As the organic solvent to be used, the hydrophilic organic solvents are preferred. Usable as the organic solvent are, for example, ketones (e.g. acetone), ethers (e.g. tetrahydrofuran), lower alcohols (e.g. methanol, ethanol, etc.), esters (e.g. ethyl acetate, etc.), hydrocarbons (e.g. benzene), amides (e.g. N,N-dimethylformamide), nitriles (e.g. acetonitrile) and halogenated hydrocarbons (e.g. methylene chloride). HCl may be used in the form of an aqueous hydrochloric acid solution or in the form of a solution in any of the solvents mentioned above or, alternatively, gaseous hydrogen chloride may be blown into a solution or suspension of SCE-2787 (crystalline or amorphous) in water or an organic solvent. As another successful way to react HCl with SCE-2787, gaseous hydrogen chloride is reacted directly with SCE-2787 in a solid state. In the above manner, the reaction between SCE-2787 and HCl in the presence of water and an organic solvent or without solvent takes place immediately. The time required for crystallization may vary depending upon the amounts of water, organic solvent and HCl used, among others. For achieving a high yield, it is desirable and preferable to spend about 5 minutes to 24 hours for crystallization.

As a production method using an organic solvent, more preferably, the SCE-2787(HCl) crystals according to the invention can be produced generally by dissolving or suspending SCE-2787 crystals in water and adding hydrogen chloride or hydrochloric acid, or dissolving SCE-2787 directly in hydrochloric acid, then adding an organic solvent to cause crystallization and collecting the resulting crystals by such means as filtration. The organic solvent solvate obtained in that manner can be converted to the organic solvent-free SCE-2787(HCl) crystal form by subjecting said solvate to an adequate organic solvent removal procedure. As mentioned above, it is also a more preferable method to blow gaseous hydrogen chloride to SCE-2787 in a solid state, i.e. without being dissolved or suspended in a solvent. According to the method it is advantageously unnecessary to effect organic solvent removal procedure. More specifically, the method for producing SCE-2787 (HCl) without employing organic solvents can be generally carried out by bringing a gas containing gaseous HCl in a concentration of about 0.01% (by weight, hereinafter w/w percent is meant by "%" unless otherwise specified) to about 3%, preferably about 0.05% to about 2%, into SCE-2787 in a solid state. The preferred gas to be used for diluting HCl gas is exemplified by carbon dioxide or nitrogen. In this method, SCE-2787 in crystalline form is preferably used as the starting material.

As a more preferable method employing an organic solvent, the organic solvent solvates of SCE-2787(HCl) can be prepared in the following manner. In the case of acetone solvate, for instance, SCE-2787 (crystalline) is suspended in ⅓ to 10 parts by weight, desirably ⅓ to 2 parts by weight, relative to one part by weight of SCE-2787, of water, 1 to 5 equivalent of hydrochloric acid is added for dissolution of SCE-2787 and, then, acetone is added in an amount 2-6 times, preferably 3-5 times, the amount of water used to thereby cause the acetone solvate of SCE-2787(HCl) to crystallize out. The thus-obtained acetone solvate of SCE-2787(HCl) generally contains 0.5 to 1 equivalent of acetone. In the case of ethanol solvate, the ethanol solvate of SCE-2787(HCl) is preferably crystallized out from the above-mentioned hydrochloric acid solution of SCE-2787 with ethanol, which is used in an amount 2-5 times, desirably 2-3 times, the amount of water used in said hydrochloric acid solution. The thus-obtained ethanol solvate of SCE-2787(HCl) generally contains 0.5 to 1.5 equivalent of ethanol. Furthermore, the solvates corresponding to ethanol, methanol, tetrahydrofuran, ethyl acetate, benzene, N,N-dimethylformamide and the like solvents mentioned above can be 2787(HCl), which can be obtained efficiently in the above manner, in the respective organic solvents. Also, the ethanol solvate can be produced by passing the nitrogen gas saturated with ethanol into the acetone solvate.

The solvates of SCE-2787(HCl) thus obtained each shows crystallinity as confirmed by powder X-ray diffraction. The SCE-2787(HCl) solvates obtained have high purity and good stability.

On the other hand, it is desirable that the organic solvent solvates among the solvates obtainable in the above manner should be deprived of the organic solvents prior to their use in pharmaceutical compositions. However, ordinary vacuum drying, for instance, can hardly eliminate the solvents to a satisfactory extent without causing decomposition of SCE-2787(HCl) itself. In accordance with the invention, this problem can be overcome and such solvents can be removed efficiently by using the supercritical fluid extraction method using carbon diode or the like or the humidification method, without increasing the temperature. After solvent removal, the product SCE-2787(HCl) may be dried by a conventional method of drying, such as vacuum drying or air-drying. The SCE-2787 solvates, such as SCE-2787(HCl) acetone solvate or SCE-2787(HCl) ethanol solvate, can be deprived of the solvents by supercritical fluid extraction using, for example carbon dioxide, in the manner mentioned below. Solvent elimination can be effected also by the humidification method by passing humidified air or nitrogen having a relative humidity of 50 to 90%, desirably 60 to 80%, through the solvates in a per se known conventional manner. The thus-obtained SCE-2787(HCl) products show crystallinity as evidenced by powder X-ray diffraction The supercritical fluid extraction is carried out by charging an extraction vessel with the cephalosporin compound in the solid form and passing supercritical carbon dioxide through the same either continuously or intermittently to thereby cause the solvent contained in the solid cephalosporin compound to be extracted with supercritical carbon dioxide. The extractor to be used in the practice of the invention is preferably a pressure vessel and generally has a temperature adjusting mechanism. It is necessary that the pressure vessel should be usable at least at the critical pressure of carbon dioxide, namely 75.3 kg/cm$^2$ (absolute pressure), generally within the pressure range of 100 to 500 kg/cm$^2$. The shape of the extractor is not critical. A vertical-type cylindrical vessel equipped with a gas inlet nozzle, a gas outlet nozzle and a nozzle or lid for charging and taking out the solid cephalosporin compound is preferred, however. It is necessary that the extractor should have a mechanism for holding the solid cephalosporin compound therein. Said mechanism can be selected from among various types depending on the grain size of the solid cephalosporin compound and corrosiveness operability in charging and discharging and economic features of the equipment. For instance, a system most suited for the purpose can be chosen from the following: a system comprising a perforated plate provided in the bottom portion of the vessel and covered with a filter cloth or wire gauze (e.g. stainless steel wire gauze) for holding said solid compound, a system comprising a porous sintered metal (e.g. stainless steel) or ceramic filter, and a system comprising a cylindrical vessel having a wire gauze (e.g. stainless steel wire gauze) or filter cloth spread on the bottom, which vessel is to be placed in an extractor after filling with the solid cephalosporin compound.

Figure 2:
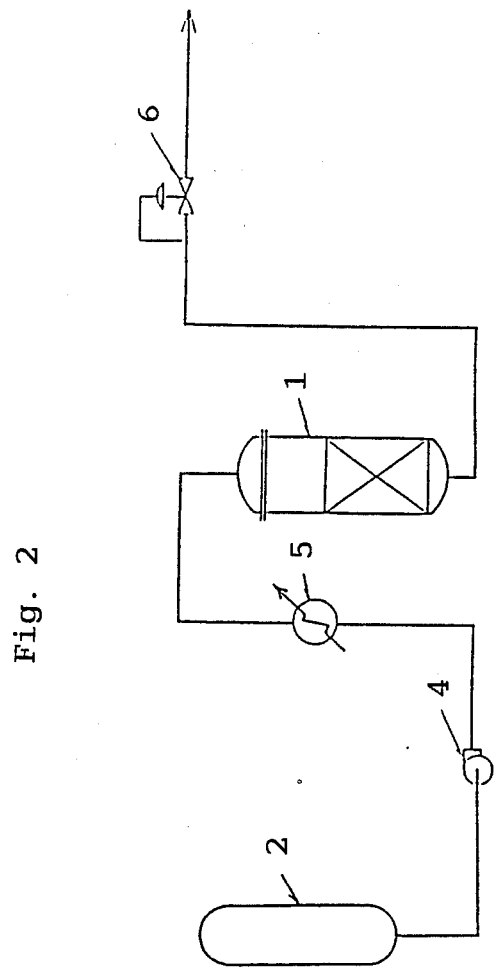

Two examples of the equipment to be used in the practice of the invention, which are most simple, are shown in FIG. 1 and FIG. 2.

FIG. 1 and FIG. 2 are described below.
1---Extractor
2---Carbon dioxide cylinder
3---Condenser
4---High-pressure metering pump
5---Heater
6---Pressure adjusting valve FIG. 1

Carbon dioxide fed from the carbon dioxide cylinder 2 is liquefied in the condenser 3 and pumped under pressure by means of the high-pressure metering pump 4. It is heated to a prescribed temperature in the heater 5, whereby it is converted to supercritical carbon dioxide, which then enters the extractor 1 filled in advance with the solid cephalosporin compound. The supercritical carbon dioxide comes into contact with the solid cephalosporin compound and extracts the residual solvent therefrom and, thereafter, is exhausted from the apparatus via the pressure-adjusting valve 6. FIG. 2

Liquefied carbon dioxide is fed from the carbon dioxide cylinder 2 directly to the high-pressure metering pump 4, in which it is pressurized and from which it is pumped to the heater 5 for conversion to supercritical carbon dioxide. The subsequent behavior is the same as described above referring to FIG. 1

In FIG. 1 and FIG. 2, supercritical carbon dioxide enters the extractor 1 at the top and flows down therethrough. The reverse direction of flow may also be used. In this case, it is preferable to provide a filter in the upper part of the vessel or in the close vicinity of the outlet of the vessel so that loss of the powdery cephalosporin compound and choking up of the piping and/or valve in the exhaustion line can be prevented.

Supercritical carbon dioxide to be used in accordance with the invention should preferably have a temperature not lower than the critical temperature 31.1° C. and a pressure not lower than the critical pressure 75.3 kg/cm$^2$ (absolute pressure).

The temperature of supercritical carbon dioxide to be used in accordance with the invention may be at any level not lower that the critical temperature of carbon dioxide (31.1° C.) but should preferably be within the range of about 35° to about 50° C. from the viewpoint of temperature controllability, heat stability of the cephalosporin compound and so on. The pressure of supercritical carbon dioxide may be at any level not lower than the critical pressure of carbon dioxide (75.3 kg/cm$^2$, absolute pressure) but, from the viewpoints of pressure controllability and economy, among others, should preferably be within the range of about 80–300 kg/cm$^2$ (absolute pressure). The flow rate of supercritical carbon dioxide is not critical but, generally, should suitably be within the range of about 0.5 to 50 kg/hour per kilogram of the solid cephalosporin compound.

Conditions similar to those employed in the conventional solvent removing method by humidification may also be used. Thus, supercritical carbon dioxide may be used in a humidified state, or the moisture content of the solid cephaloporin compound may be adjusted before the solvent removal operation is conducted. For instance, solvent removed may be carried out with supercritical carbon dioxide containing about 0.1 to 5% (w/w %) of water vapor, or after humidifying the solid cephalosporin compound to a moisture content of 5 to 50% (w/w %) based on the yield of cephalosporin compound after drying.

When the cephalosporin compound contains a plurality of solvents, these solvents may be removed simultaneously. The solid cephalosporin compound is preferably used in the form of a powder prepared in advance by grinding.

According to the humidification method, organic solvent removal can be effected in the conventional manner by passing humidified air or nitrogen having a relative humidity of 50 to 90%, desirably 60 to 80%, through the organic solvent solvate of SCE-2787(HCl).

The thus-obtained SCE-2787(HCl) shows crystallinity as evidenced by powder X-ray diffraction analysis.

Figure 4:
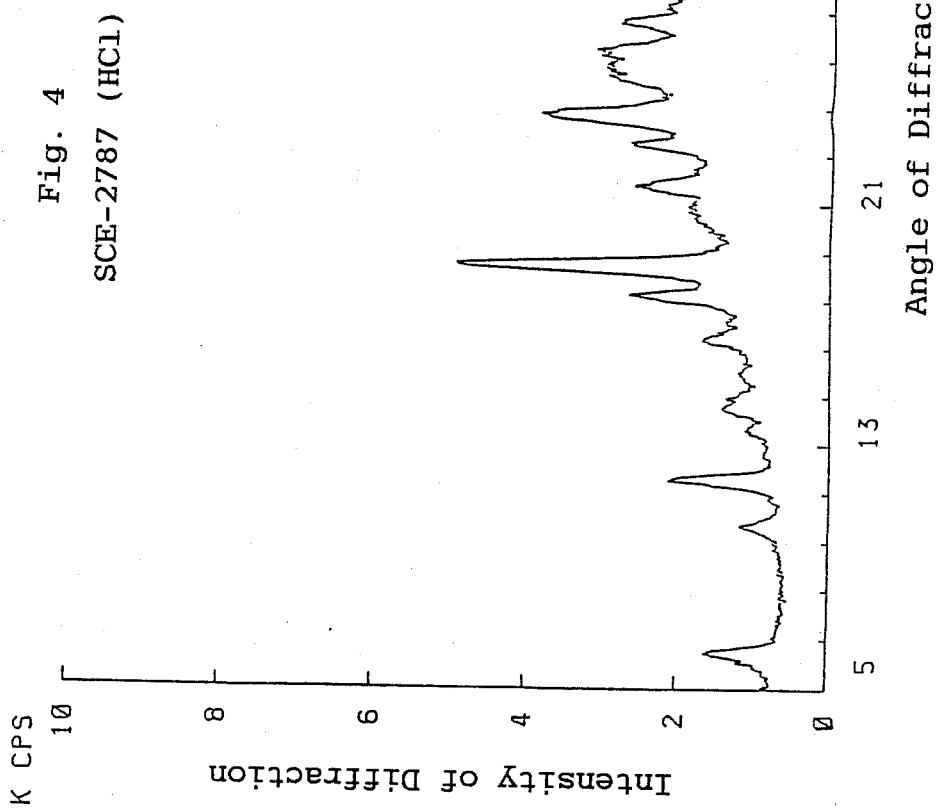
Figure 5:
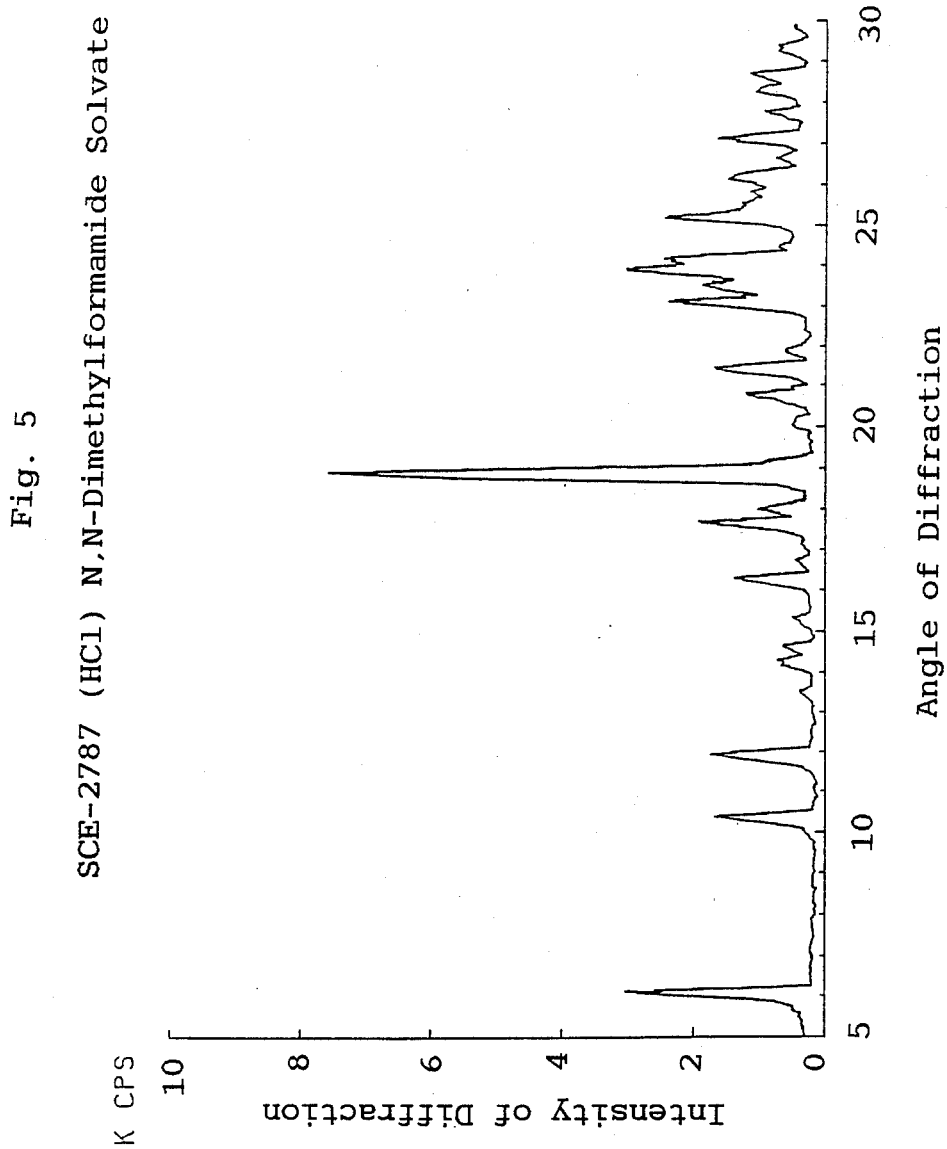

The powder X-ray diffraction patterns of the crystals of Reference Examples 17, 19 and 14 (CuK$\alpha$, 50KV, 100mA; CuK$\alpha$, 40KV, 70mA; CuK$\alpha$, 50KV, 100mA; respectively) as the representative forms of crystals of SCE-2787(HCl) are shown in FIG. 4, 5 and 6, respectively.

The pharmaceutically acceptable water-soluble basic substance to be used in accordance with the invention includes, but is not limited to, alkali metal or alkaline earth metal carbonates, such as sodium hydrogen carbonate and sodium carbonate, other inorganic bases than carbonates, such as disodium phosphate and dipotassium phosphate, and organic bases, such as methylglucamine, tri(hydroxymethyl)-aminomethane and L-arginine. In short, any of the nontoxic basic substances used in the field of chemistry can be suitably used in the practice of the invention.

Among them, particularly preferred are alkali metal carbonates (e.g. sodium carbonate, sodium hydrogen carbonate).

The quantity ratio between SCE-2787(HCl) and the pharmaceutically acceptable water-soluble basic substance is advisably such that the equivalent ratio between HCl (hydrogen chloride), which is a constituent of SCE-2787(HCl), and the nontoxic basic substance amounts generally to about 1:0.5 to about 1:5.0, preferably about 1:1.2 to about 1:3.0, more preferably about 1:1.4 to about 1:2.0.

Therefore, monoacid bases such as sodium hydrogen carbonate and methylglucamine are advisably used generally in an amount of about 0.5 to 2.5 moles, preferably about 1.2 to 2.0 moles, per mole of SCE-2787(HCl), whereas diacid bases such as sodium carbonate are used generally in an amount of about 0.25 to 2.50 moles, preferably about 0.6 to 1.5 moles, per mole of SCE-2787(HCl).

The antibiotic composition according to the invention can be prepared by combining SCE-2787(HCl) with a pharmaceutically acceptable water soluble basic substance in the above-mentioned quantity ratio by per se known means. Per se known drug additives, for example a local anesthetic such as lidocaine hydrochloride or mepivacaine hydrochloride, may be incorporated in said composition in amounts which will not impair the effects of the invention, if addition of such additives is desired. SCE-2787(HCl), pharmaceutically acceptable water-soluble basic substance and other components are each used generally in the powder or crystalline form and, accordingly, the composition according to the invention generally occurs as a solid.

When, in accordance with the invention, SCE-2787(HCl) and a carbonate are filled into vials, for instance, the vials after filling thereof are generally evacuated and then sealed (hereinafter sometimes referred to briefly as vacuum-sealed). When the vials are stored in that state, oxidative degradation can be prevented and, in addition, it is easy to pour a solvent, such as distilled water for injection, isotonic sodium chloride solution or saline or an aqueous solution of a local anesthetic, into the vials prior to use. Upon addition of such solvent to the vials, carbon dioxide gas is generated and the rate of dissolution of the principal active ingredient is remarkably increased. Such mode of storage in vials is particularly preferred since rapid dissolution is possible in the state in which the vials are allowed to stand still. Furthermore, in that case, the vial inside space is filled with the carbon dioxide gas generated and, therefore, the SCE-2787 solution obtained can advantageously be stored stably without undergoing oxidative degradation even after dissolution. Prior to sealing, the vials are evacuated generally to about 0 to 500 mmHg, preferably about 0 to 100 mmHg. The solvent is added generally in an amount of about 1 to 100 ml per gram of SCE-2787 (10 mg/ml to 1 g/ml).

When an inorganic base other than the carbonate or an organic base is used, for instance, SCE-2787(HCl) may be added to a solvent containing such base to give SCE-2787(HCl) solution. In this case, the SCE-2787(HCl) solution is generally sterilized by filtration and then filled into containers. Said solution may also be subjected to lyophilization, for instance. The thus-obtained lyophilized preparation for injection can be readily dissolved prior to use by pouring distilled water for injection, isotonic sodium chloride solution or saline or an aqueous solution of a local anesthetic into the containers. Such solvent is added generally in an amount of about 1 to 100 ml per gram of SCE-2787, like the case of combination with a carbonate.

Thus, the antibiotic composition of the present invention is improved in solubility, particularly free of change of solubility after dissolution, and stable in storage. Besides, when used for injectable solution, the solution does not cause any local actions or hemolytic actions.

Also, the SCE-2787(HCl) solution obtainable in this manner can be used as a bactericide for external use, for example as a disinfectant for surgical devices and equipment, hospital rooms, drinking water and so forth. Furthermore, said solution can be administered to warm-blooded animals, such as human, mouse, rat and dog, by instramuscular or intravenous injection as a therapeutic agent for infectious diseases caused by gram-positive or gram-negative bacteria.

For use as an external-use bactericide for surgical devices and equipment, an aqueous solution having an SCE-2787 concentration of about 100 $\mu$g/ml may be prepared and sprayed over surgical devices and equipment. For the treatment of urinary tract infections caused by *Escherichia coli* in men or mice, an SCE-2787(HCl) solution may be administered by intramuscular or intravenous injection at a dosage of about 5 to 50 mg (as SCE-2787) per kilogram, preferably in three or four divided doses per day. In a mode of practice of the invention, the antibiotic composition can be supplied, for example, by using a vial such as shown in FIG. 3.

Figure 3:
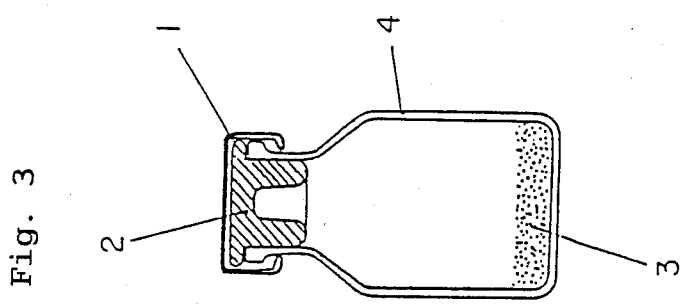

That is, FIG. 3 shows a mode of practice of the invention in which the antibiotic composition according to the invention is contained in a vacuum-sealed vial. In FIG. 3, the reference numeral 1 indicates an aluminum cap, 2 a rubber closer, 3 the composition according to the invention, and 4 the vial.

The following working examples and reference examples illustrate the invention in further detail. It is to be understood, however, that they are by no means limitative of the scope of the present invention.

In the following reference examples, the stability data given are the residual percentages determined by high-performance liquid chromatography after storing under the respective conditions described for the period described.

REFERENCE EXAMPLE 1

Production of SCE-2787 (crystalline) from SCE-2787 (amorphous)

In 400 ml of distilled water was dissolved 100 g of the lyophilized product SCE-2787(amorphous) obtained by following the procedure described in Japanese Kokai Tokkyo Koho No. 62-149682 (European Patent Appln. Laid-Open No. 203291), Example 13, and crystallization was induced by stirring at room temperature for 1.5 hours. The resultant crystals were collected by filtration, washed with 100 ml of distilled water and dried under reduced pressure to give 77.6 g of SCE-2787 (crystalline).

Elemental analysis:
Calculated for $C_{19}H_{179}S_2O_5''3.3H_2$ I. O: C, 39.69; H, 4.14; N, 21.92; S, 11.15
Found: C, 39.81; H, 3.88; N, 21.92; S, 11.45.

REFERENCE EXAMPLE 2

Production of SCE-2787 (crystalline) from SCE-2787 solution in hydrochloric acid In 300 ml of distilled water was suspended 56.6 g of the SCE-2787 (crystalline) obtained in Reference Example 1. Then, 100 cc of 1 N hydrochloric acid was added for causing dissolution of the crystals. The resultant solution was adjusted to pH about 4 with anhydrous sodium carbonate. Crystallization was caused by allowing the mixture to stand at room temperature for 3 hours with occasional shaking. The thus-obtained crystals were washed with 150 ml of distilled water and dried under reduced pressure to give 42.4 g of SCE-2787 (crystalline).

REFERENCE EXAMPLE 3

Production of SCE-2787(HCl) (amorphous)

In 20 ml of distilled water was suspended 515 mg of the SCE-2787 (crystalline) obtained in Reference Example 1, 1 ml of 1 N hydrochloric acid was added, and SCE-2787(HCl) (amorphous) was obtained by lyophilization. The moisture content of this product was 3.5%.

Elemental analysis:
Calculated for $C_{19}H_{18}N_9ClO_5S_2 \cdot 2.5H_2O$: C, 38.22; H, 3.88; N, 21.11; Cl, 5.94
Found: C, 38.04; H, 4.05; N, 21.26; Cl, 5.87

The stability of this product as determined after 1 week of storage at 40° C. was 94% in terms of residual percentage.

REFERENCE EXAMPLE 4

Crystals of acetone solvate of SCE-2787(HCl) from SCE-2787

In 20 ml of 1 N hydrochloric acid was dissolved 11.3 g of the SCE-2787 (crystalline) obtained in Reference Example 1, then 77 ml of acetone was added slowly with stirring. After seed crystals as obtained in Example 13 mentioned hereafter were added, the resultant mixture was stirred at room temperature for 7 hours to cause crystallization. The resultant crystals were collected by filtration, washed with 20 ml of a mixture of acetone and water (6:1) and further with 40 ml of acetone, and air-dried under blowing to give 7.6 g of acetone-solvates SCE-2787(HCl).

This product had a moisture content of 2.6% and an acetone content of 8.0% (0.85 mole). The stability data for this product as determined after 8 days of storage at 40° C. and 60° C. were 98% and 97%, respectively, in terms of residual percentage.

REFERENCE EXAMPLE 5

Crystals of acetone solvate of SCE-2787(HCl) from SCE-2787

In 240 ml of 3 N hydrochloric acid was dissolved 138.4 g of the SCE-2787 (crystalline) obtained in Reference Example 1. Acetone (720 ml) was then added slowly with stirring. After seed crystals as obtained in Example 13 mentioned hereafter were added, the resultant mixture was stirred at room temperature for 2 hours for causing crystallization. Furthermore, 360 ml of acetone was added dropwise over 1 hour and, after completion of the dropping, the resultant mixture was stirred for 4 hours for further crystallization. The resultant crystals were collected by filtration, washed with 195 ml of a mixture of acetone and water (6:1) and further with 480 ml of acetone, and dried by exposure to a dried air stream to give 126.6 g of acetone-solvates SCE-2787(HCl). This product had a moisture content of 5.3% and an acetone content of 7.3% (0.8 mole).

REFERENCE EXAMPLE 6

Crystals of ethanol solvate of SCE-2787(HCl) from SCE-2787

In 30 ml of 2N hydrochloric acid was dissolved 11.2 g of the SCE-2787 (crystalline) obtained in Reference Example 1. Ethanol (60 ml) was then added slowly with stirring, and the resultant mixture was stirred at room temperature for 30 hours to effect crystallization. The resultant crystals were collected by filtration and washed with 50 ml of a mixture of ethanol and water (4:1). After further washing with 50 ml of ethanol, the crystals were dried by exposure to a dried air stream to give 5.8 g of ethanol-solvates SCE-2787(HCl). This product had a moisture content of 4.8% and an ethanol content of 8.6% (1.2 moles).

REFERENCE EXAMPLE 7

Crystals of ethanol solvate of SCE-2787(HCl) from acetone solvate of SCE-2787

In 30 ml of ethanol was suspended 3.0 g of the acetone-solvates SCE-2787(HCl) obtained in Example 2, and the suspension was stirred for 4.5 hours. The resultant crystals were collected by filtration, washed with 35 ml of ethanol, dried by exposure to a dried air stream and further dried under reduced pressure to give 2.8 g of ethanol-solvates SCE-2787(HCl). This product had a moisture content of 3.0% and an ethanol content of 7.5% (1.0 mole). NMR spectromertry of this product failed to demonstrate the presence of acetone. The stability data for this product as determined after 8 days of storage at 40° C. and 60° C. were 98% and 98%, respectively, in terms of residual percentage.

REFERENCE EXAMPLE 8

Crystals of methanol solvate of SCE-2787(HCl) from acetone solvate of SCE-2787(HCl)

A suspension of 1 g of the acetone-solvates SCE-2787(HCl) obtained in Example 2 in 10 ml of methanol was stirred at room temperature for 6 hours. The crystals thus obtained were washed with 5 ml of methanol and dried by exposure to a dried air stream to give 890 mg of methanol-solvates of SCE-2787of (HCl). This product had a moisture content of 3.1%. NMR spectroscopy revealed that the methanol content was about 1 mole and that acetone was absent.

REFERENCE EXAMPLE 9

Crystals of N,N-dimethylformamide solvate of SCE-2787(HCl) from acetone solvate of SCE-2787(HCl)

A suspension of 1 g of the acetone-solvates SCE-2787(HCl) obtained in Example 2 in 10 ml of N,N-dimethylformamide was stirred at room temperature for 6 hours. The crystals thus obtained were washed with 5 ml of N,N-dimethylformamide and dried by exposure to a dried air stream to give 625 mg of N,N-dimethylformamide-solvates SCE-2787(HCl). This product had a moisture content of 2.3%. NMR spectroscopy showed that about 1 mole of N,N-dimethylformamide was contained in the product. The presence of acetone was not indicated. The powder X-ray diffraction pattern of this product is shown in FIG. 5.

REFERENCE EXAMPLE 10

Solvent removal from acetone solvate of SCE-2787(HCl) by supercritical fluid extraction The acetone-solvates SCE-2787(HCl) obtained in Example 2 was charged into a vertical-type cylindrical vessel having a diameter of 25 mA and a height of 50 mA and equipped in the lower part thereof with a filter plate. Extractive removal of acetone was effected by passing carbon dioxide through the powder layer from the top to the bottom of the vessel (flow rate: 2 liters per minute, on the standard conditions basis) while the vessel outside temperature and the fluid inlet temperature were adjusted to 40° C. and the pressure within the vessel was adjusted to 200 kg/cm². (The equipment shown in FIG. 1 was used.)

The product had a moisture content of 3.7%. Gas chromatography indicated that the content of residual acetone was 0.5%.

II(KBr)cm$^{-1}$: 1787

NMR (DMSO-d$_6$): 3.48 (2H, dd, J =26.1, 18.9 Hz), 3.87 (3H, s), 5.17 (1H, d, J =5.4 Hz), 5.50 (2H, broad s), 5.85 (1H, dd, J =9.0, 5.4 Hz), 8.04 (1H, dd, J =9.0, 4.5 Hz), 8.41 (1H, d, J =1.8 Hz), 8.41 (1H, d, J =1.8 Hz), 8.85 (1H, d, J =1.8 Hz), 8.98 (1H, d, J =9.0 Hz), 9.11 (1H, d, J =4.5 Hz)

REFERENCE EXAMPLE 11

Solvent removal from ethanol solvate of SCE-2787(HCl) by supercritical fluid extraction Four grams of the ethanol solvate of SCE-2787(HCl) as obtained in Example 3 was subjected to solvent removal in the same manner as in Example 7 to give 3.5 g of SCE-2787(HCl). This product had a moisture content of 2.7%. Gas chromatography indicated that the content of residual ethanol was 0.1% or less. This product gave an NMR spectrum which was substantially the same as that obtained with the product of Example 7. The stability data for said product as determined after 3 weeks of storage at 40° C. and 60° C. were 98%, and 94%, respectively, in terms of residual percentage.

REFERENCE EXAMPLE 12

Organic solvent removal from acetone solvate of SCE-2787(HCl) by humidification

A 5.0-g portion of the acetone solvate of SCE-2787(HCl) as obtained in Example 2 was spread over a glass filter, and solvent removal was effected by passing through the filter and solvate layer a stream of air humidified by passing through a water layer maintained at 10° C. (flow rate: 1 liter per minute). The solvent removal product was then dried under reduced pressure to give 4.85 g of SCE-2787(HCl). This product had a moisture content of 8.2%. NMR spectroscopy revealed that the content of residual acetone was not more than 0.2%. This product gave an NMR spectrum which was essentially the same as that obtained in Example 7.

Elemental analysis:
Calculated for $C_{19}H_{18}N_9ClO_5S_2 \cdot 2.5H_2O$: C, 38.22; H, 3.88; N, 21.11; Cl, 5.94
Found: C, 38.17; H, 3.56; N, 21.02; Cl, 5.96

REFERENCE EXAMPLE 13

Solvent removal from ethanol solvate of SCE-2787(HCl) by humidification

A 4.0-gram portion of the ethanol solvate of SCE-2787(HCl) as obtained in Example 4 was placed on a glass filter and deprived of the solvent by passing through the filter and solvate layer a stream of air humidified by passing through a saturated aqueous solution of sodium acetate to give 3.0 g of SCE-2787(HCl). Gas chromatography showed that the resultant product had a residual ethanol content of 0.1% or less. The thus-obtained SCE-2787(HCl) was dried under reduced pressure. The dried product was tested for its stability under various moisture conditions. The residual percentage data obtained after 1 week or 5 weeks of storage at 40° C. or 60° C. are shown below in the table.

| Moisture content | After 1 week | | After 5 weeks | |
|---|---|---|---|---|
| | 40° C. | 60° C. | 40° C. | 60° C. |
| 2.9% | 97% | 96% | 97% | 92% |
| 1.6% | 100% | 98% | 98% | 94% |
| 0.8% | 99% | 97% | 98% | 95% |

REFERENCE EXAMPLE 14

Conversion of crystals of SCE-2787 to crystals of SCE-2787(HCl) using HCl gas diluted in nitrogen Crystals of SCE-2787 (2.5 g, moisture content 2.4%) as obtained in accordance with Reference Example 1 were filled in a vertical-type cylindrical glass filter of 25 mm in diameter. Through the layer of the crystals was passed from the upper side of the vessel vertically for 25 hours a stream of 0.1% HCl gas, which was prepared by mixing 1% HCl gas (diluted in nitrogen) at the flow rate of 200 ml/min, and nitrogen gas at the flow rate of 1,800 ml/min and then was passed through a U-shaped tube filled with calcium chloride for drying to give crystals of SCE-2787(HCl). The thus-obtained crystals were further exposed to nitrogen gas flow for 11 hours to give crystals of SCE-2787(HCl) showing the powder X-ray diffraction pattern as shown in FIG. 6.

REFERENCE EXAMPLE 15

Conversion of crystals of SCE-2787 to crystals of SCE-2787 (HCl) using HCl gas diluted in carbon dioxide Crystals of SCE-2787 (2.5 g, moisture content 9.1%) as obtained in accordance with Reference Example 1 (CuXα, 50KV, 100mA) were filled in the same glass as Reference Example 14. Through the layer of the crystals was passed from the upper side of the vessel vertically for 20 hours a stream of 0.1% HCl gas which was prepared by mixing 1% HCl gas (diluted in nitrogen) at the flow rate of 800 ml/min and carbon dioxide gas at the flow rate of 7,200 ml/min and then was passed through a U-shaped tube filled with calcium chloride for drying to give crystals of SCE-2787(HCl). The thus-obtained crystals were further exposed to carbon dioxide gas flow for 12 hours to give crystals of SCE-2787(HCl). This product was found to contain 3-6% moisture and 1.0 mol of HCl according to the analysis by way of high performance liquid chromatography and silver nitrate titration.

REFERENCE EXAMPLE 16

In 1 ml of 1N-HCl was dissolved 563 mg of SCE-2787 (crystalline), and the solution was concentrated under reduced pressure to half the volume. N,N-Dimethylformamide (1 ml) was added to the residue, which dissolved. While the solution was being stimulated with a spatula, 5 ml of acetone was added to the solution dropwise slowly. Continual stimulus charged to the solution at room temperature caused slowly crystallization. Observation with polarizing microscope indicated that this product had crystallinity. On the other hand, 563 mg of SCE-2787 (crystals) was dissolved in 1N-HCl, and 4 ml of acetone was added slowly to the solution with stirring. Addition of the crystals as obtained above as the seed crystals to the mixture at room temperature caused gradual crystallization. The resulting crystals were collected by filtration under reduced pressure, and the collected crystals were washed with acetone and dried under reduced pressure to give 280 mg of the crystals of SCE-2787(HCl) as the acetone solvate. This product had a moisture content of 2.6% and an acetone content of 8.0%.

REFERENCE EXAMPLE 17

Solvent removal from ethanol solvate of SCE2787(HCl) by humidification

A 3.0-gram portion of the crystals of the ethanol solvate of SCE-2787(HCl) (ethanol content: 9.9%, moisture content: 0.83%), as produced in accordance with the method analogous to that of Reference Example 7 was placed on a vertical-type cylindrical glass filter of 25 mm in diameter and deprived of the solvent by passing through the filter and solvate layer a stream of nitrogen gas humidified by passing through a water layer at 18° C/., for 3 hours to give 3.0 g of the crystals of SCE-2787(HCl) showing a powder X-ray diffraction pattern as shown in FIG. 4. This product had a moisture content of 13.7%, and gas chromatography showed that the content of the residual ethanol was not more than 0.01%.

EXAMPLE 1

A 35-ml vial was filled with 1.07 g of SCE-2787(HCl) and 152.2 mg of anhydrous sodium carbonate. The vial was vacuum-sealed at 50 mmHg. When 3 ml of distilled water for injection was added to the vial, dissolution took place very easily. After the lapse of 24 hours following dissolution, any change in solubility, such as insoluble matter precipitation, was not observed.

EXAMPLE 2

A 17-ml vial was filled with 0.54 g of SCE-2787(HCl) and 99.1 mg of anhydrous sodium carbonate. The vial was vacuum-sealed at 50 mmHg. When 3 ml of physiological saline of the pharmacopeia grade was added to the vial, the contents were dissolved very easily. Even at 24 hours after dissolution, any change in solubility, such as insoluble matter precipitation, was not observed.

EXAMPLE 3

A 35-ml vial was filled with 1.07 g of SCE-2787(HCl) and 241.1 mg of anhydrous sodium hydrogen carbonate. The vial was vacuum-sealed at 2 mmHg. When 20 ml of distilled water for injection was added to the vial, dissolution took place very easily. Even at 24 hours after dissolution, any change in solubility, such as insoluble matter precipitation, was not observed.

EXAMPLE 4

A 9-ml vial was filled with 0.268 g of SCE-2787(HCl) and 60.3 mg of anhydrous magnesium carbonate. The vial was vacuum-sealed at 20 mmHg. When 3 ml of distilled water for injection was added to the vial, dissolution took place very easily. Even at 24 hours after dissolution, any change in solubility, such as insoluble matter precipitation, was not observed.

EXAMPLE 5

To a solution of 56.0 g of methylglucamine in 200 ml of distilled water for injection was added 107.1 g of SCE-2787(HCl). The mixture was stirred for effecting dissolution and then diluted to 300 ml (total volume) with distilled water for injection. After sterilization by filtration, the solution was filled into 17-ml vials in an amount of 1.5 ml per vial. The vial contents were lyophilized to give an injectable preparation. When 3 ml of distilled water for injection was added to the vial, dissolution took place very easily. Even at 24 hours after dissolution, any change in solubility, such as insoluble matter precipitation, was not observed.

EXAMPLE 6

To a solution of 74.4 g of disodium phosphate dodecahydrate in 150 ml of distilled water for injection was added 107.1 of SCE-2787(HCl)·The mixture was stirred for effecting dissolution and then diluted to a total volume of 200 ml (total volume) with distilled water for injection. After sterilization by filtration, the solution was filled into 9-ml vials in an amount of 0.5 ml per vial. THe vial contents were then lyophilized to give an injectable preparation. When 3 ml of distilled water for injection was added to the vial, dissolution took place very easily. Even at 24 hours after dissolution, any change in solubility, such as insoluble matter precipitation, was not observed.

EXAMPLE 7

An antibiotic composition was prepared by following the procedure of Example 5 except that 34.7 g of tris(-hydroxymethyl)aminomethane was used in lieu of 56.0 g of methylglucamine. When 3 ml of distilled water for injection was added to the vial, the composition was dissolved very readily. Even at 24 hours after dissolution, any change in solubility, such as insoluble matter precipitation, was not observed.

EXAMPLE 8

A 17-ml vial was filled with 1.07 g of SCE-2787(HCl) and 164.5 mg of anhydrous sodium carbonate. The vial was vacuum-sealed at 50 mmHg. When 3 ml of distilled water for injection was added to the vial, dissolution took place very easily. After the lapse of 24 hours following dissolution, any change in solubility, such as insoluble matter precipitation, was not observed.

EXAMPLE 9

A 17-ml vial was filled with 1.07 g of SCE-2787(HCl) and 164.5 mg of anhydrous sodium carbonate. The vial was vacuum-sealed at 50 mmHg. When 3 ml of aqueous solution of mepivacaine hydrochloride was added thereto dissolution took place very easily. Even after the lapse of 24 hours following dissolution, any change in solubility, such as insoluble matter precipitation, was not observed.

EXAMPLE 10

A 130-ml vial was filled with 1.07 g of SCE-2787(HCl) and 164.5 g of anhydrous sodium carbonate. The vial was vacuum-sealed at 10 mmHg. When 100 ml of saline was added for dissolution, dissolution took place very easily. Even at 24 hours after dissolution, any change in solubility, such as precipitation of insoluble matter, was not observed.

EXAMPLE 11

A 2-ml ampoule was filled with 321 $\mu$g of SCE-2787(HCl), 49.4 $\mu$g of anhydrous sodium carbonate and 9 mg of sodium chloride. The ampoule was sealed. When 1 mg of distilled water for injection was added to the vials for dissolution, dissolution took place very easily, Even at 24 hours after dissolution, any change in solubility, such as precipitation of insoluble matter, was not observed.

What we claim is:

1. An antibiotic composition which comprises an effective antibacterial amount of 7β-[(Z)-2-(5-amino-1,2,4-thiadiazol-3-yl)-2(Z)-methoxyiminoacetamido]-3-(1-imidazo[1,2-b]pyridazinium)methyl]-3-cephem-4-carboxylate hydrochloride and a pharmaceutically acceptable [water-soluble basic substance] alkali metal carbonate in an equivalent ratio of about 1:1.2 to about 1:3.0 relative to said hydrochloride.

2. An antibiotic composition as claimed in claim 1 wherein the alkali metal carbonate is sodium carbonate.

3. An antibiotic composition as claimed in claim 1 wherein the alkali metal carbonate is sodium hydrogen carbonate.

4. An antibiotic composition as claimed in claim 1 which comprises the pharmaceutically acceptable water-soluble basic substances in an amount of about 1.4 to 2.0 equivalent relative to one equivalent of 7μ-[(Z)-2-(5-amino-1,2,4-thiadiazol-3-yl)-2(Z)-methoxyiminoacetamido]-3-(1-imidazo[1,2-b]pyridazinium)methyl]-3-cephem-4-carboxylate hydrochloride.

* * * * *